United States Patent [19]

DeWald et al.

[11] Patent Number: 4,792,548

[45] Date of Patent: Dec. 20, 1988

[54] TRANS-BENZOPYRAN-(4,3-B)-1,4-OXAZINE DERIVATIVES, INTERMEDIATES AND PHARMACEUTICAL USE

[75] Inventors: Horace A. DeWald; Lawrence D. Wise, both of Ann Arbor, Mich.

[73] Assignee: Warner-Lambert Company, Morris Plains, N.J.

[21] Appl. No.: 865,306

[22] Filed: May 21, 1986

[51] Int. Cl.[4] .................. A61K 31/535; C07D 498/04
[52] U.S. Cl. .................................. 514/229.8; 544/101
[58] Field of Search ................. 544/101; 514/227, 239

[56] References Cited

FOREIGN PATENT DOCUMENTS 80117 6/1983 European Pat. Off. .
161218 11/1985 European Pat. Off. .

OTHER PUBLICATIONS

Hackh's Chemical Dictionary, McGraw-Hill, New York (1969) p. 62.
J. Med. Chem., 1985, 28 367–375.
J. Med. Chem., 1985, 28, 215–225.

*Primary Examiner*—Richard L. Raymond
*Attorney, Agent, or Firm*—Ronald A. Daignault

[57] ABSTRACT trans-Benzopyran-4,3b-1,4-oxazines are described as well as methods of preparation. The compounds are presynaptic dopamine agonists and may be used in pharmaceutical composition form for treating psychoses, e.g., schizophrenia.

15 Claims, No Drawings

TRANS-BENZOPYRAN-(4,3-B)-1,4-OXAZINE DERIVATIVES, INTERMEDIATES AND PHARMACEUTICAL USE

BACKGROUND OF THE INVENTION

Octahydrobenzo[g]quinolines have been recently described in J. Med. Chem., 1985, 28, 367-375 as dopamine agonists. Resolved monophenolic 2-aminotetralins and 1,2,3,4,4a,5,6,10b-octahydrobenzo[f]quinolines and their structural and stereochemical isomers have been studied for central acting pre- and postsynaptic dopamine-receptor agonist activity. For example, the compound of the formula

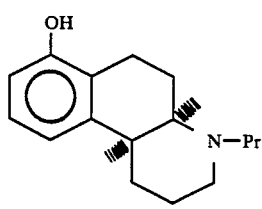

among others is described in J. Med. Chem., 1985, 28, 215-225.

Benzo-(pyrano and thiopyrano)-pyridines of the formula

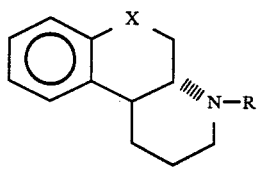

where X is oxygen or sulfur and R is hydrogen, alkyl or arylalkyl have also been described as presynaptic dopamine-receptor agonists in European patent publication No. 161218.

The present benzopyrano oxazine compounds have been found to have presynaptic dopamine-receptor agonist activity and as such are useful in the treatment of Parkinsons's disease or as an antipsychotic agent, for example in the treatment of schizophrenia.

SUMMARY OF THE INVENTION

Accordingly, the present invention relates to a compound of the formula

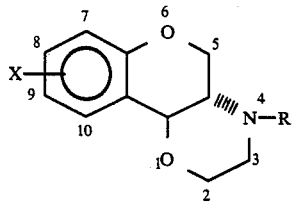

I wherein R is hydrogen, lower alkyl or aryllower alkyl; X is hydroxy, lower alkyl, lower alkoxy, halogen, or benzyloxy, or a pharmaceutically acceptable acid addition salt thereof.

The present invention also relates to a pharmaceutical composition comprising an effective amount of a compound of Formula I or a pharmaceutically acceptable acid addition salt thereof with a pharmaceutically acceptable carrier.

The present invention further relates to a method of treating Parkinson's disease or psychoses, e.g., schizophrenia, in a subject suffering therefrom comprising administering to said subject an effective amount of a pharmaceutical composition containing a compound of Formula I or a pharmaceutically acceptable acid addition salt thereof in unit dosage form.

DETAILED DESCRIPTION

In the compounds of Formula I, the term "lower alkyl" means a straight or branched alkyl group having from one to six carbon atoms such as, for example, methyl, ethyl, propyl, isopropyl, butyl, sec-butyl, tert-butyl, amyl, isoamyl, neopentyl, hexyl, and the like.

The term "aryllower alkyl" incorporates the above definition for "lower alkyl" while "aryl" is defined herein as phenyl or phenyl substituted by lower alkyl, lower alkoxy, hydroxy, halogen, or trifluoromethyl. The phenyl radical may be mono-, di- or tri-substituted, but preferably mono- or disubstituted.

Halogen represents fluorine, chlorine, bromine, or iodine.

Lower alkoxy is O-lower alkyl of from one to six carbon atoms as defined above for "lower alkyl."

By the compounds of the present invention, there exists the possibility of both geometric isomers, cis- and trans-. The trans-isomer is preferred.

The compounds of the present invention also contain an asymmetric carbon atom which results in a racemic mixture of racemate as well as individual optical isomers, enantiomers. The compounds of the present invention can be resolved into their individual enantiomers by known resolution methods and include the individual enantiomers.

The compounds of the invention form pharmaceutically acceptable acid addition salts with organic and inorganic acids. Examples of suitable acids for salt formulation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with a sufficient amount of the desired acid in the convention manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated foams, with pharmaceutically acceptable solvents such as water, ethanol, and the like are equivalent to the unsolvated forms for purposes of the invention.

The ring system for the compounds of Formula I is numbered as follows

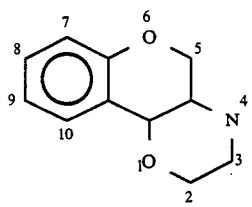

Thus, a preferred embodiment of the present invention is a compound of Formula I where in X is hydroxy, alkoxy or benzyloxy attached to the 7- or 9-position of the ring system.

Another preferred embodiment is a compound of Formula I wherein R is hydrogen, lower alkyl, or phenyl lower alkyl.

Still another preferred embodiment is a compound of Formula I wherein R is hydrogen, n-propyl, n-butyl or phenethyl, and X is methyl, methoxy, hydroxy, or fluoro, or a pharmaceutically acceptable acid addition salt thereof.

Especially valuable are the compounds of Formula I, wherein X is as defined above and R is n-propyl.

Particularly valuable is trans-9-hydroxy-3,4,4a,10b-tetrahydro-4-propyl-2H,5',uns/H/ -[1]benzopyrano[4,3-b]-1,4-oxazine, or a pharmaceutically acceptable acid addition salt thereof.

The compounds of the present invention and of Formula I may be prepared by reduction of a compound of the formula

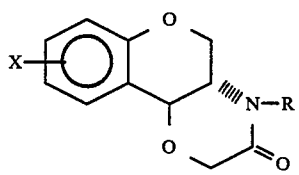

wherein X and R are as defined above for compounds of Formula I, and, if desired, converting the resulting product when X is lower alkoxy or benzyloxy to a compound where X is hydroxy by known means, and, if further desired, converting the resulting free base to a pharmaceutically acceptable acid addition salt thereof by known means.

The above chemical reduction consists in reducing the amide group with a hydride reducing agent such as lithium aluminum hydride or diborane. The reaction is carried out under known conditions in standard anhydrous solvents, such as ethers, e.g., diethyl ether or tetrahydrofuran.

When it is desired to convert a compound of Formula I where X is lower alkoxy to a corresponding compound where X is hydroxy the reaction is preferably carried out with 40% hydrobromic acid and then neutralized.

Conversion of a compound of Formula I where X is benzyloxy to a corresponding compound where X is hydroxy can also be carried by the above method, but preferably, is carried by catalytic hydrogenation with, for example, palladium on carbon catalyst at low pressures and temperatures.

Intermediates of Formula II are also new and are part of the present invention. They may be prepared by reacting a compound of the formula

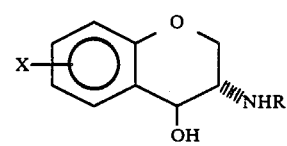

wherein R and X are as defined above, with a haloacetyl halide, e.g., chloroacetyl chloride to form an α-haloamide derivative, which in turn, is ring closed with base to afford a compound of Formula II

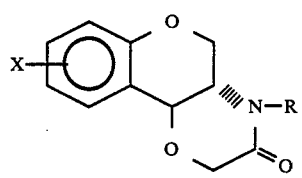

Starting materials of the Formula III are known or, if new, may be prepared from known benzopyranones, 1, according to a method described in Chem. Pharm. Bull, 25, 859 (1977) and illustrated by the following reaction sequence.

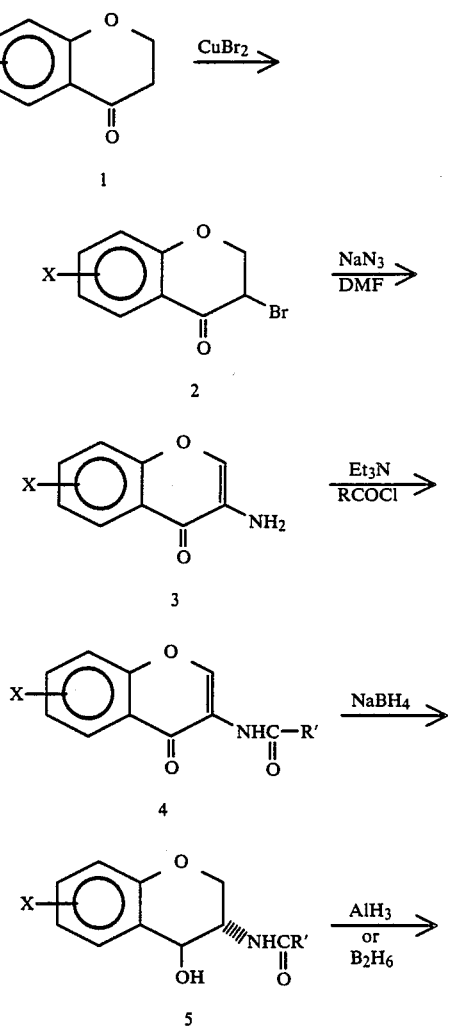

-continued

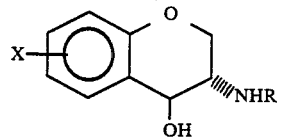

III

The compounds of the present invention are new chemical substances which are useful as pharmaceutical agents for the treatment of psychoses such as, for example, schizophrenia.

The compounds of the present invention decrease the firing rate of dopaminergic neurons and decrease dopamine metabolites which are indicative of dopamine agonists. As such the compound are also useful for treating Parkinson's disease.

Thus, for example, trans-9-hydroxy-3,4,4a,10b-tetrahydro-4-propyl-2H,5H-[1]benzopyrano-[4,3-b]-1,4-oxazine, a representative compound of the present invention causes a significant decrease in firing rate of dopaminergic neurons and a significant decrease in dopamine metabolites.

The compounds of the present invention can be prepared and administered in a wide variety of oral and parenteral dosage forms. It will be obvious to those skilled in the art that the following dosage forms may comprise as the active component, either a compound of Formula I, a corresponding pharmaceutically acceptable salt of a compound of Formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low-melting wax, cocoa butter, and the like. The term "preparation" is intended to include the formulation of the active compound with encapsulating material as carrier providing a capsule in which the active compound (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as antipsychotic agents, the compounds utilized in the pharmaceutical method of this invention are administered at the initial dosage of about 0.1 mg to about 10 mg per kilogram daily. A daily dose range of about 1.0 mg to about 10 mg per kilogram is preferred.

The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1 trans-9-Methoxy-3,4,4a,10b-tetrahydro-4-propyl-2H,5H-[1]benzopyrano-[4,3-b]-1,4-oxazine NaBH$_4$ (1.6 g; 0.04 mol) was added to a stirred solution of 3 g (0.011 mol) of trans-4a,10b-dihydro-9-methoxy-4-propyl-2H,5H-[1]benzopyrano[4,3-b]-1,4-oxazine-3-4H-one in 75 ml tetrahydrofuran under nitrogen; then 5.6 g (0.04 mol) of boron trifluoride etherate was added at slow droprate. After stirring at room temperature overnight, excess reagent was destroyed by the slow addition of 5 ml of acetic acid. Most of the THF solvent was evaporated and replaced by 150 ml of dichloromethane. The mixture was stirred with 70 ml of 3N sodium hydroxide. The organic layer was separated, washed with brine, dried over anhydrous MgSO$_4$ and the solvent evaporated in vacuo. The residue (3 g) was crystallized as its hydrochloride salt by treatment with 20% isopropanolic.HCl and dilution with ethyl acetate. The salt metls at 250°–255° C.

EXAMPLE 2

Reduction of compounds of Formula II where X is 7-ethoxy, 9-fluoro, 7,8-dimethyl and 8,10-dimethyl by the procedure described in Example 1 gave the corresponding compounds of Formula I.

EXAMPLE 3 trans-9-Hydroxy-3,4,4a,10b-tetrahydro-4-propyl-2H,5H-[1]benzopyrano-[4,3-b]-oxazine A solution of 4 g (0.015 mol) of the product of Example 1 in 300 ml of dichloromethane was cooled to 5° C., and under $N_2$, 8 g (0.03 mol) of boron tribromide was added dropwise with stirring. Stirring was continued an hour at 5° C., then 2.5 hours at 25° C. To the stirred mixture was added 80 ml of 6N ammonium hydroxide. The organic layer was separated, dried over $MgSO_4$, and the solvent was evaporated. The dark residue was dissolved in 70 ml of 1N sodium hydroxide, treated with Darco and filtered. The filtrate was acidified with concentrated HCl then the pH adjusted to eight with buffer. The mixture was filtered to collect 1.2 g of hygroscopic brown solid. The crude product was purified by crystallization of the hydrochloride salt from 20% isopropanolic.HCl and ethyl acetate, 0.3 g, mp 220° dec.

In a similar manner, trans-7-hydroxy-3,4,4a,10b-tetrahydro-4-propyl-2H,5H-[1]benzopyrano-[4,3-b] was obtained by cleavage of the corresponding 7-ethoxy compound of Example 2.

EXAMPLE 4

General Procedure for the Preparation of trans-4a,10b-dihydro-4-propyl-2H,5H-[1]-benzopyrano[4,3-b]-1,4-oxazine-3(4H)-ones Chloroacetyl chloride (4 g; 0.04 mol) was added dropwise to a stirred mixture of 5 g (0.02 mol) of trans-3,4-dihydro-6-methoxy-3-(propylamino)-2H-1-benzopyran-4-ol hydrochloride in 200 ml dichloromethane and 40 ml of water containing 5 g of sodium hydroxide. After stirring two hours at 25° C., the mixture was diluted with 100 ml of water. The organic layer was separated, dried ($MgSO_4$) and evaporated to give 6 g (90%) of the intermediate chloroacetamide, mp 116°–118° C. from ether, trans-2-chloro-N-(3,4-dihydro-4-hydroxy-6-methoxy-2H-1-benzopyrano-3-yl)-N-propyl acetamide.

The chloroacetamide (5.5 g, 0.0175 mol) was dissolved in 200 ml of 2-propanol and treated dropwise with a solution of 1 g of potassium hydroxide in 2 ml of water. After stirring at 25° C. for two hours, the mixture was treated with 5 ml of 20% isopropanolic HCl and evaporated in vacuo. The residue was dissolved in $CH_2Cl_2$, washed with water, and the solvent evaporated to give 4.8 g (93%) of the above titled compound with a methoxy group at the nine-position, mp 118° C. from ether.

EXAMPLE 5

General Procedure for the Preparation of the trans-3,4-dihydro-3-(propylamino)-2H-1-benzopyran-4-ols from 2,3-dihydro-4H-1-benzopyran-4-ones

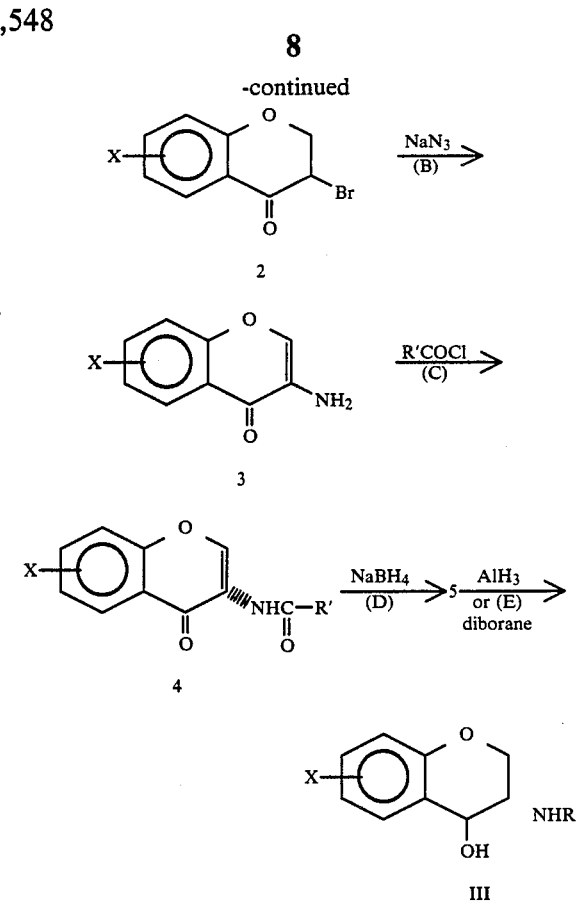

For purposes of illustration, X is 6-methoxy and R is propyl:

(a) A solution of 16 g (0.09 mol) 2,3-dihydro-6-methoxy-4H-1-benzopyran-4-one in 125 ml of chloroform was added dropwise to a stirred refluxing ethyl acetate solution (125 ml) of cupric bromide (25 g). After stirring under reflux for two hours, the mixture was filtered, and the filtrate was evaporated in vacuo. The residue was taken up into dichloromethane and washed free of excess bromine salts with aqueous sodium sulfite. The organic solution was evaporated in vacuo to yield 20.5 g of 3-bromo-2,3-dihydro-6-methoxy-4H-1-benzopyran-4-one.

(b) A solution of 14.3 g (0.055 mol) of the above compound in (a) in 75 ml of dimethylformamide (DMF) was treated with 4 g (0.06 mol) of sodium azide with stirring. A mild exotherm ensued to 45° C. After stirring another one hour at 40°–45° C., the mixture was poured into 300 ml of water. Extraction of the mixture with ethyl acetate, and evaporation of the solvent gave 10 g (95%) of 3-amino-6-methoxy-1-benzopyran-4-one, mp 98°–100° C. from ethyl acetate-pet. ether.

(c) A solution of 8.5 g (0.044 mol) of the compound in (b) in 150 ml dichloromethane and 8 ml triethylamine was treated dropwise with 5 g (0.05 mol) of propionyl chloride at 20°–25° C. After standing overnight, the mixture was stirred with a saturated aqueous solution of sodium bicarbonate. The organic layer was separated, dried ($MgSO_4$) and evaporated to give 6.8 g (68%) of N-(6-methoxy-4-oxo-4H-1-benzopyran-3-yl)propanamide.

(d) To a stirred suspension of 6.5 g (0.026 mol) of the compound in (c) in 200 ml of ethanol was added 10 g (0.25 mol) of sodium borohydride in portions. After stirring in 25° C. for 20 hours, the solution was concen-

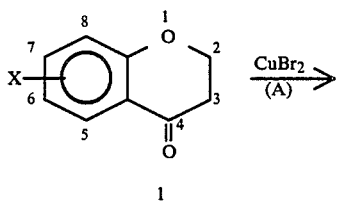

trated and diluted with 300 ml dichloromethane and 200 ml of 1N sodium hydroxide. The organic layer was separated, dried (MgSO₄) and evaporated in vacuo to give 6 g (90%) of trans-N-(3,4-dihydro-4-hydroxy-6-methoxy-2H-1-benzopyran-3-yl)propanamide.

(e) Sodium borohydride (6 g, 0.15 mol) was added in portions under nitrogen to a stirred solution of 12 g (0.05 mol) of the compound in (d) in 200 ml of tetrahydrofuran. This was followed by the dropwise addition of 21 g (0.15 mol) of boron trifluoride.etherate. After stirring 18 hours at 25° C., the mixture was treated with about 15 ml of acetic acid and concentrated in vacuo. The residue was stirred 0.5 hour in a mixture of 300 ml dichloromethane and 150 ml of 3N sodium hydroxide. The organic layer was separated, dried over MgSO₄, and the solvent was evaporated in vacuo to yield 10.4 g of solid which was crystallized as the hydrochloride salt of trans-3,4-dihydro-6-methoxy-3-(propylamino)-2H-1-benzopyran-4-ol from isopropanolic.HCl and ethyl acetate, 9.9 g (71%), mp 185° dec.

What is claimed is:

1. A compound of the formula

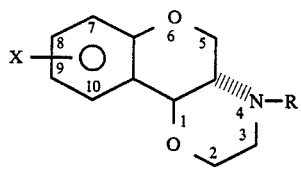

wherein R is hydrogen, lower alkyl, phenyl lower alkyl or phenyl lower alkyl in which phenyl is substituted by lower alkyl, lower alkoxy, hydroxy, halogen, or trifluoromethyl; X is hydroxy, lower alkyl, lower alkoxy, halogen, or benzyloxy, or a pharmaceutically acceptable acid addition salt thereof.

2. A compound according to claim 1, wherein X is hydroxy, alkoxy, or benzyloxy in the 7- or 9-positions.

3. A compound according to claim 1, wherein R is hydrogen, lower alkyl or phenyl lower alkyl.

4. A compound according to claim 3, wherein R is hydrogen, n-propyl, n-butyl, or phenethyl.

5. A compound according to claim 1, wherein X is hydroxy, methyl, methoxy or fluoro.

6. A compound according to claim 2, wherein R is hydrogen, n-propyl, n-butyl, or phenethyl, and X is hydroxy, methoxy, or benzyloxy.

7. A compound according to claim 5, wherein R is n-propyl.

8. A compound according to claim 6, wherein R is n-propyl.

9. A compound according to claim 8, and being trans-9-hydroxy-3,4,4a,10b-tetrahydro-4-propyl-2H,5H-[1]-benzopyrano[4,3-b]-1,4-oxazine, or a pharmaceutically acceptable acid addition salt thereof.

10. A pharmaceutical composition comprising an anti-psychotic effective amount of a compound according to claim 1 or a pharmaceutically acceptable acid addition salt thereof with a pharmaceutically acceptable carrier or diluent.

11. A method of treating psychoses in a subject suffering therefrom comprising administering to said subject a composition according to claim 10 in unit dosage form.

12. A compound of the formula

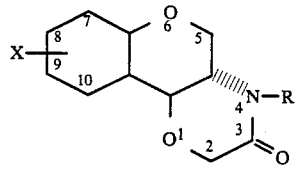

wherein R is hydrogen, lower alkyl, phenyl lower alkyl or phenyl lower alkyl in which phenyl is substituted by lower alkyl, lower alkoxy, hydroxy, halogen, or trifluoromethyl, and X is hydroxy, lower alkyl, lower alkoxy, halogen, or benzyloxy.

13. A compound according to claim 12, wherein R is hydrogen, lower alkyl or phenyl lower alkyl, and X is hydroxy, methyl, methoxy or fluoro.

14. A compound according to claim 13, wherein R is n-propyl.

15. A compound according to claim 14, and being trans-4a,10b-dihydro-6-methoxy-4-propyl-2H,5H-[1]-benzopyrano[4,3-b]-1,4-oxazine-3(4H)-one.

* * * * *

UNITED STATES PATENT AND TRADEMARK OFFICE
CERTIFICATE OF CORRECTION

PATENT NO. : 4,792,548
DATED : December 20, 1988
INVENTOR(S) : HORACE A. DeWALD and LAWRENCE D. WISE It is certified that error appears in the above—identified patent and that said Letters Patent is hereby corrected as shown below:

In column 10, line 25, delete "  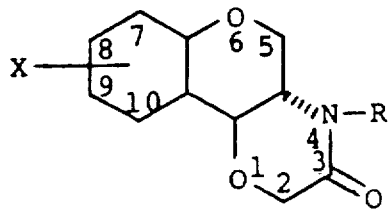  "  and insert

--  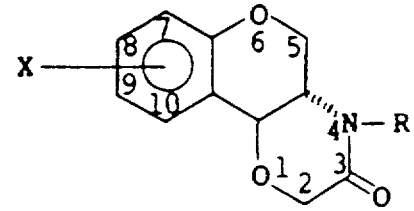  --.

Signed and Sealed this

Sixteenth Day of May, 1989

Attest:

DONALD J. QUIGG

Attesting Officer

Commissioner of Patents and Trademarks